United States Patent [19]

Takino et al.

[11] 3,946,012
[45] Mar. 23, 1976

[54] 6-L-DIHYDROXYETHYL-2,4,7-TRIOXO-8-D-RIBITYL PTERIDINE AND PROCESS FOR PRODUCING THE SAME

[75] Inventors: Masuichi Takino, Nara; Teikichi Kurosaki; Munehiko Odaka, both of Osaka, all of Japan

[73] Assignee: Nippon Zoki Pharmaceutical Co., Ltd., Osaka, Japan

[22] Filed: Sept. 13, 1973

[21] Appl. No.: 396,810

[30] Foreign Application Priority Data
Sept. 13, 1972 Japan.............................. 47-91907

[52] U.S. Cl......... 260/251.5; 260/256.4 C; 424/251
[51] Int. Cl.².......................................... C07D 475/02
[58] Field of Search................................ 260/251.5

[56] References Cited
OTHER PUBLICATIONS

Rowan et al. –J. Chem. Soc. (c), 1968 (4), 452–458.
Pfleiderer –C.A. 52, 18458fg (1958).
McNutt –C.A. 54, 8836d (1960).
Pfleiderer et al. –C.A. 54, 21113–21114 (1960).
Nuebel et al. –C.A. 57, 8569–8571 (1962).
Mitsuda et al. –C.A. 59, 5501e (1963).
Lohrmann et al. –C.A. 60, 9343d (1964).
Kishi et al. –C.A. 69, 59203w (1968).
Suzuki et al. –C.A. 75, 95610j (1971).
Matsuura et al. –C.A. 79, 5523p (1973).

*Primary Examiner*—Raymond V. Rush
*Attorney, Agent, or Firm*—Stewart and Kolasch

[57] ABSTRACT

Trioxopteridine derivatives of the formula

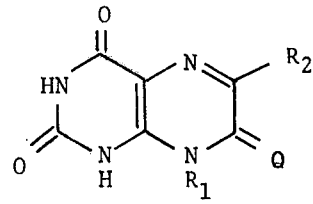

, wherein $R_1$ is a normal alkyl group having 0 to 6 hydroxyl groups and $R_2$ is hydrogen or a normal lower alkyl group having 0 to 5 hydroxyl groups, are prepared by catalytically hydrogenating a 6-substituted-5-nitro-2,4-dioxopyrimidine to give a 6-substituted-5-amino-2,4-dioxopyrimidine, and then reacting the latter compound with a compound of the formula $R_2$—A—COOR$_3$, wherein $R_3$ is hydrogen, lower alkyl, an alkali metal or an alkaline earth metal and A is carbonyl or a group of the formula

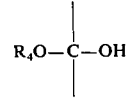

wherein $R_4$ is lower alkyl. The resulting trioxopteridine derivatives have analgesic and antiphlogistic properties and are therefore useful as pharmaceutical medicaments.

1 Claim, No Drawings

6-L-DIHYDROXYETHYL-2,4,7-TRIOXO-8-D-RIBITYL PTERIDINE AND PROCESS FOR PRODUCING THE SAME

BACKGROUND OF THE INVENTION

The present invention relates to novel trioxopteridine derivatives and to processes for producing such compounds. More particularly, the invention relates to novel compounds having the following general formula:

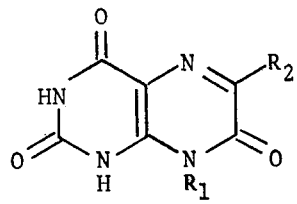

wherein $R_1$ is a normal (straight chain) alkyl group having 0 to 6 hydroxyl groups, and $R_2$ is a hydrogen atom or a normal lower alkyl group having 0 to 5 hydroxyl groups.

The pharmaceutical industry is constantly striving to find and develop new compounds having various useful properties. In particular, such compounds must be safe and effective and without side effects. The present invention provides novel compounds having useful pharmaceutical properties.

One of the objects of the present invention is to provide novel trioxopteridine derivatives.

Another object of the invention is to provide an effective method for producing said compounds.

A further object of the invention is to provide novel compounds which are useful in combatting rheumatoid arthritis, arthralgia, frozen shoulders, chronic arthritis and like ailments.

These and other objects and advantages of the present invention will become apparent to those skilled in the art from a consideration of the following specification and claims.

SUMMARY OF THE INVENTION

In accordance with the present invention, the novel trioxopteridine derivatives (IV) are prepared by catalytically hydrogenating a 6-substituted-5-nitro-2,4-dioxopyrimidine of the formula:

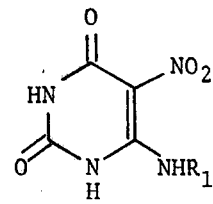

to give a 6-substituted-5-amino-2,4-dioxopyrimidine having the formula:

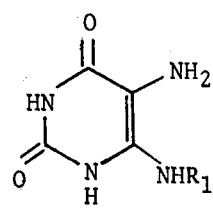

and then reacting said 6-substituted-5-amino-2,4-dioxopyrimidine with a compound of the formula:

$$R_2-A-COOR_3 \qquad (III)$$

wherein $R_3$ is a hydrogen atom, a straight- or branched-chain lower alkyl group, an alkali metal atom or an alkaline earth metal atom. A represents a carbonyl group or a group of the formula:

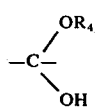

wherein $R_4$ is a lower alkyl group. The term "lower alkyl" in the present application refers to alkyl groups having from 1 to 5 carbon atoms.

Hence, the reaction sequence employed in the present invention may be shown as follows (where I-a and II-a are the tautomers of I and II, respectively):

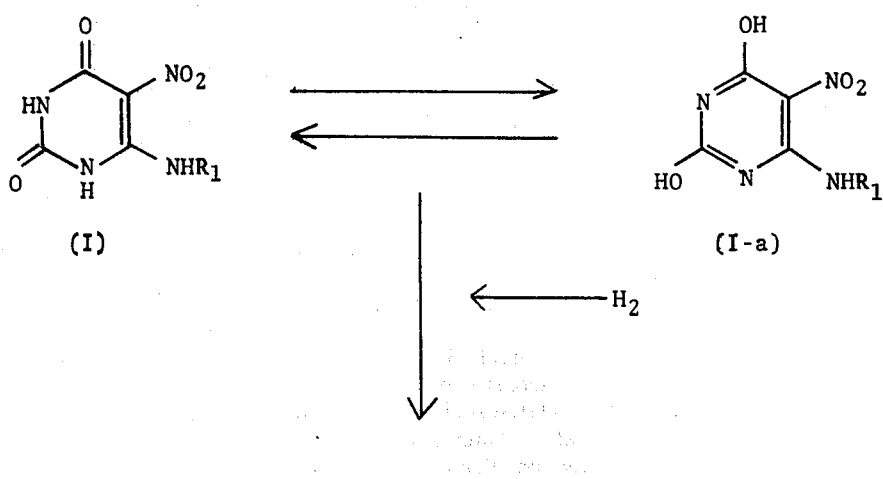

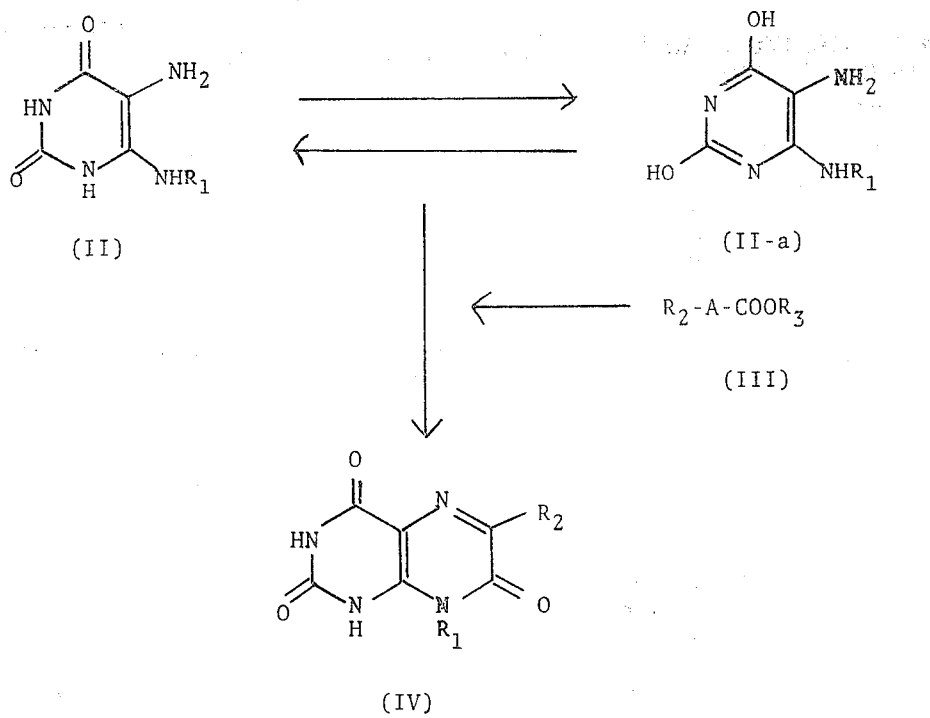

More specifically, $R_1$, $R_2$, $R_3$ and $R_4$ in the above formulae represent, for example, the following groups.

$R_1$ may be methyl, ethyl, propyl, butyl, pentyl, hexyl, heptyl, hydroxymethyl, 2-hydroxyethyl, 2,3-dihydroxypropyl, 3,4-dihydroxybutyl, 2,3-dihydroxybutyl, 2,3,4-trihydroxybutyl, 2,3,4,5-tetrahydroxypentyl, 2,3,4,5,6-pentahydroxyhexyl, 2,3,4,5,6,7-hexahydroxyheptyl and other straight chain alkyl groups of 1 to 7 carbon atoms. Some of these groups contain asymmetric atoms or optical isomers, however, their isomers and mixtures thereof may be equally used effectively in the present invention.

$R_2$ is hydrogen or methyl, ethyl, propyl, butyl, hydroxymethyl, dihydroxyethyl, 1-hydroxyethyl, 1,2-dihydroxypropyl, trihydroxypropyl, tetrahydroxybutyl, pentahydroxypentyl and other straight chain lower alkyl groups having 0 to 5 hydroxyl groups. Some of these groups include optical isomers, however, such isomers and mixtures thereof are equally used in this invention.

$R_3$ represents, for example, methyl, ethyl, propyl, isopropyl, butyl, isobutyl and other straight- or branched-chain lower alkyl groups; sodium, potassium and other alkali metal atoms; and calcium, barium and other alkaline earth metal atoms.

$R_4$ is a straight or branched-chain lower alkyl such as methyl, ethyl, propyl or butyl.

Instead of using the compounds of formula (I) and formula (II), it is quite suitable and advantageous to use the tautomers represented by formula (I-a) and formula (II-a), respectively, in the reactions in the present invention. It is readily apparent that the quantity proportion of the mixture of tautomers to be employed depends on the specific reaction conditions, for example, the pH value of the solvent used in the reaction process, etc.

The hydrogenation of compound (I) is generally carried out under normal or increased pressure in the presence of a hydrogenation catalyst such as palladium, platinum oxide, Raney nickel or Raney cobalt. Water and/or an organic solvent, e.g., an alkanol, can be used in the reaction, and the reaction proceeds completely at room temperature even when water is employed.

The acid addition salts of compound (II) that are produced by the reaction of compound (I) with the inorganic or organic acid are quite stable. The compound (II) produced in the hydrogenation reaction sometimes includes some unstable products mixed therewith, however, even if only the catalyst is filtered therefrom, the solution can be reacted directly with compound (III) without separating the unstable products from the solution. It is desirable to carry out the filtration of the catalyst in an inert gas such as nitrogen, for example, under the pressure of nitrogen gas. In reacting compound (II) with compound (III), a liquid controller, for example, a weakly acidic alkali metal salt such as sodium acetate or potassium acetate, or ammonia is advantageously used for accelerating the velocity of the reaction. When a slightly unstable material such as 5-amino-2,4-dioxo-6D-ribitylaminopyrimidine is involved in the reaction, the addition of an antioxidant such as an alkali metal salt, e.g., potassium disulfite, to the reaction mixture affords good results in the reaction.

The reaction is preferably conducted at a temperature of from about 0° to 100°C., and it is advantageous to start the reaction at a lower temperature and then to raise the temperature of reaction by heating during the course of the reaction process. In this way, the reaction proceeds selectively without destroying the configuration of the substituted radicals $R_1$ and $R_2$ because of the comparatively lower reaction temperature used at the beginning of the reaction.

Compound (IV) may be easily crystallized by methods well known in the art, such as concentration of the reaction solution under reduced pressure, or by the addition of crystallizing solvents to the reaction solution, and then purified by means of magnesium silicate column chromatography or anion exchange resin chromatograpahy.

The novel compound (IV) of the present invention possesses analgesic and antiphlogistic activity. Accordingly, this compound is particularly useful as a remedy for rheumatoid arthritis, arthralgia, frozen shoulders, chronic arthritis and like disorders.

The trioxopteridine derivatives of the present invention can be readily formulated into a pharmaceutical composition by means well known in the art. For example, unit dosages of the compound may be mixed with conventional pharmaceutically acceptable, inert diluents, carriers or adjuvants. In this manner the compounds can be formulated as a tablet, capsule, syrup, elixir or injectable solution, as desired. For instance, an excipient such as the sugar lactose may be used with the trioxopteridine derivative in sufficient quantity to form a capsule or to form a powder which can be added to an aqueous solution to form a syrup.

EXAMPLES OF THE INVENTION

The following Examples are given merely as illustrative of the present invention and are not to be considered as limiting.

EXAMPLE 1

4.0 g of 6-L-arabitylamino-5-nitro-2,4-dioxopyrimidine dissolved in 150 ml of water is hydrogenated in the presence of a palladium active-carbon catalyst at room temperature. After adding 30 ml of 1N hydrochloric acid thereto, an aqueous solution of 5-amino-6-L-arabitylamino-2,4-dioxopyrimidine is obtained by the filtration of said catalyst from the resulting solution in a nitrogen atmosphere. Without isolation of the reaction product, the obtained solution is heated together with 2.0 g of ethyl pyruvate and 4.4 g of sodium acetate at 80°C. for 20 minutes. After filtering out the crystals produced by cooling the solution in an ice bath, the crystals are dissolved in 100 ml of water at a pH of 9.0 by means of heating. Then, this solution is adjusted to a pH of 1.0 with 6N hydrochloric acid to obtain a crystalline product by filtration. By crystallization from 300 ml of water, 2.8 g of dried pale yellow needle crystals of 8-L-arabityl-6-methyl-2,4,7-trioxopteridine is obtained.

Yield: 65.0%

M.P.: 289.0° – 290.5°C (with decomposition)

Analysis - calculated for $C_{12}$ $H_{16}$ $N_4$ $O_7$: Theory: C, 43.90; H, 4.91; N, 17.07%; Found: C, 44.29; H, 4.91; N, 16.90%

Specific rotary power: $[\alpha]_D^{20}$ + 12.60 (C=0.230, in pH 8.0 buffer solution of phosphoric acid)

pKa value: 3.60 ± 0.02, 12.93 ± 0.02

EXAMPLE 2

1.0 g of 5-nitro-2,4-dioxo-6-D-xylytyl-aminopyrimidine is dissolved in 50 ml of water and adjusted to a pH of 10 with 7.5N ammonia water. The resulting compound in this solution is reduced in a hydrogen atmosphere in the presence of palladium catalyst. After the reaction is completed, 15 ml of 1N hydrochloric acid is added to the resultant solution. Then, the catalyst in the solution is filtered off under pressurized nitrogen gas to obtain 5-amino-2,4-dioxo-6-D-xylytylaminopyrimidine and to this filtrate is added 0.75 g of ethylglyoxylate hemi-acetal. After adjustment to a pH of 5 with 2.2 g of sodium acetate, the precipitate is obtained by filtration. The precipitate is dissolved in 6 ml of 1N aqueous sodium hydrogen carbonate. The solution is concentrated to dryness under reduced pressure and is then dissolved in 3 ml of water by means of heating. The solution is kept under cold storage and is obtained to in crystalline material. After the crystalline material is recrystallized from 90% ethanol (pH 1.5) and then from water, 0.46 g of crystals of 2,4,7-trioxo-8-D-xylytylpteridine is obtained.

Yield: 44.8%

M.P.: 250.0° – 251.5°C

Analysis - calculated for $C_{11}$ $H_{14}$ $N_4$ $O_7$: Theory: C, 42.04; H, 4.49; N, 17.83%; Found: C, 41.93; H, 4.40; N, 17.42%

Specific rotary power: $[\alpha]_D^{20}$ + 16.40 (C=0.235, in pH 8.0 buffer solution of phosphoric acid) $[\alpha]_D^{20}$ – 1.82 (C=0.220, 0.1N-HCl)

pKa value: 3.18 ± 0.02, 12.45 ± 0.01

EXAMPLE 3

1.65 g of 6-D-lyxityl-5-nitro-2,4-dioxopyrimidine dissolved in 150 ml of water is reduced in the presence of palladium catalyst to obtain 5-amino-6-D-lyxitylamino-2,4-dioxopyrimidine and is condensed with 0.8 g ethyl pyruvate under weak acidity. After heating with stirring for 1 ½ hours, the solution is concentrated to 50 ml and adjusted to a pH of 1.0 . 200 ml of ethanol is added to the filtrate of this solution, and the solution is cooled. The resulting precipitate is recrystallized from water, and 0.85 g of pale yellow needle crystals of 8-D-lyxityl-6-methyl-2,4,7-trioxopteridine is obtained.

Yield: 48.0%

M.P.: 267.0° – 268.5°C (with decomposition)

Analysis - calculated for $C_{12}$ $H_{16}$ $N_4$ $O_7$: Theory: C, 43.90; H, 4.91; N, 17.07%; Found: C, 44.01; H, 4.89; N, 16.97%

Optical rotation: $[\alpha]_D^{20}$ – 12.99° (C=0.300, in pH 8.0 buffer solution of phosphoric acid) $[\alpha]_D^{20}$ – 4.23° (C=0.260, 0.1N-HCl)

pKa value: 3.76 ± 0.01, 13.01 ± 0.02

EXAMPLE 4

5-nitro-2,4-dioxo-6 -β-hydroxyethylaminopyrimidine is hydrogenated in the presence of Raney nickel, and the reaction product is purified to obtain 5-amino-2,4-dioxo-6-β-hydroxyethylaminopyrimidine hydrochloride. 2 g of the obtained compound and 300 mg of potassium disulfite are dissolved in 80 ml of water and to this solution is added 2 g of α-keto-D-calcium gluconate. Then the mixture is heated under reflux in a nitrogen atmosphere for one hour. After cooling, the filtrate is concentrated to 25 ml of solution. Thereafter, the solution is purified by means of magnesium silicate chromatography and strong base ion-exchange chromatography to obtain 1.0 g of 6-(D-arabo)-tetrahydroxybutyl-8-β-hydroxyethyl-2,4,7-trioxopteridine.

Yield: 32.4%

M.P.: 184° – 185°C (with decomposition)

Analysis - calculated for $C_{12}$ $H_{16}$ $N_4$ $O_8$: Theory: C, 41.86; H, 4.68; N, 16.28%; Found: C, 41.51; H, 4.39; N, 16.33%

Optical rotation: $[\alpha]_D^{20}$ – 40.8 (C=0.270, in pH 8.0 buffer solution of phosphoric acid) $[\alpha]_D^{20}$ – 47.7 (C=0.130, 0.1N-HCl)

pKa value: 3.25 ± 0.05, 12.80 ± 0.02

EXAMPLE 5

2 g of 5-nitro-2,4-dioxo-6-D-ribitylaminopyrimidine dissolved in 160 ml of water is reduced in the presence of palladium catalyst. 200 ml of filtrate is obtained by removal of the catalyst after the addition of hydrochloric acid thereto. To this solution is added 1.0 g of potassium disulfite and 5 g of α-keto-L-barium erythronate. The pH of the solution is then adjusted to pH 7.0 using sodium acetate . (3 hydrate). After refluxing in a nitrogen atmosphere for 2.5 hours, the insoluble product in the reaction solution is filtered out. The filtrate is adjusted to a pH of 1.5 and is purified by means of active carbon chromatography (extracted with 5% of pyridine solution) and magnesium silicate chromatography to obtain 0.721 g of 6-L-dihydroxyethyl-2,4,7-trioxo-8-D-ribityl pteridine.

Yield: 29.2%

M.P.: 136° – 139°C (with decomposition)

Analysis - calculated for $C_{13}H_{18}N_4O_9$: Theory: C, 41.71; H, 4.85; N, 14.97%; Found: C, 42.20; H, 4.59; N, 14.61%

Optical rotation: $[\alpha]_{320}^{22} - 5.72° \times 10^4$ (C=3.86 × $10^{-3}$, pH 8.0 buffer solution of phosphoric acid)
$[\alpha]_{320}^{22} + 4.41° \times 10^4$ (C=3.86 × $10^{-3}$, 0.1N-HCl)

pKa value: $3.36 \pm 0.03$, $12.44 \pm 0.02$

The invention being thus described, it will be obvious that the same may be varied in many ways. Such variations are not to be regarded as a departure from the spirit and scope of the invention, and all such modifications are intended to be included within the scope of the following claims.

1. The compound 6-L-dihydroxyethyl-2,4,7-trioxo-8-D-ribityl pteridine.

* * * * *